United States Patent [19]

Aigner

[11] Patent Number: 5,746,717

[45] Date of Patent: May 5, 1998

[54] BALLOON CATHETER AND DEVICE FOR PERFUSION WITH THE BALLOON CATHETER

[76] Inventor: Karl R. Aigner, Biebricher Allee 9, D-65187 Wiesbaden, Germany

[21] Appl. No.: 500,997

[22] PCT Filed: Mar. 23, 1994

[86] PCT No.: PCT/EP94/00903

§ 371 Date: Aug. 8, 1995

§ 102(e) Date: Aug. 8, 1995

[87] PCT Pub. No.: WO94/22519

PCT Pub. Date: Oct. 13, 1994

[30] Foreign Application Priority Data

Mar. 30, 1993 [DE] Germany ............ 43 10 378.2

[51] Int. Cl.[6] .................................. A61M 29/00
[52] U.S. Cl. .................... 604/102; 604/131; 604/248
[58] Field of Search ............... 604/96–103, 30, 604/32, 48, 131, 246, 248; 606/192, 194; 128/656, 658

[56] References Cited

U.S. PATENT DOCUMENTS

| | | |
|---|---|---|
| 3,394,705 | 7/1968 | Abramson . |
| 4,758,221 | 7/1988 | Jureidini ............................ 604/95 |
| 4,832,688 | 5/1989 | Sagae . |
| 4,892,519 | 1/1990 | Songer ............................ 604/96 |
| 5,147,334 | 9/1992 | Moss . |
| 5,180,366 | 1/1993 | Woods ............................ 604/96 |
| 5,295,961 | 3/1994 | Niederhauser .................... 604/96 |

FOREIGN PATENT DOCUMENTS

| | | |
|---|---|---|
| 0 383 429 | 8/1990 | European Pat. Off. . |
| 3400874 | 2/1985 | Germany . |
| 3821544 | 12/1989 | Germany . |
| WO 89/03232 | 4/1989 | WIPO . |

Primary Examiner—Corrine M. McDermott
Assistant Examiner—Deborah B. Blyveis
Attorney, Agent, or Firm—Baker & Daniels

[57] ABSTRACT

Multi-lumen balloon catheter with a closed tip and with an expandable balloon arranged at a short distance from the proximal end of the catheter, with at least one contrast marking at one location on the catheter, which marking permits a determination of the positions of the balloon, with at least two lumina extending in the longitudinal direction of the catheter, of which one communicates with the inside of the expandable balloon and the second lumen has a number of lateral openings in the catheter wall, the distance of the lateral openings increasing in the distal direction from the balloon, and the proximal opening in the side wall being arranged at a distance of 2 mm to 5 mm from the distal end of the balloon, and its use in a device for the isolated perfusion of therapeutically active substances.

19 Claims, 2 Drawing Sheets

BALLOON CATHETER AND DEVICE FOR PERFUSION WITH THE BALLOON CATHETER

BACKGROUND OF THE INVENTION

1. Field of the Invention

The present invention relates to a device for the isolated perfusion of therapeutically active substances or substance combinations. The core of the invention is in this case a multi-lumen catheter which is used for the complete or partial blocking of the blood stream of the area of the body to be treated. This interruption or reduction of the flow in a blood vessel permits the administration of locally very high concentrations of active substance which cannot be achieved with conventional techniques without harming the patient.

The administration of such high concentrations of pharmacologically active substances is a requirement which is frequently encountered in medicine. Devices which permit this are desirable in particular in the area of chemotherapy. Such a device, and an associated double-lumen catheter, are known from DE-A-3,400,874. This publication deals specifically with a double-lumen catheter for a device for in vivo purification of blood, to which device the catheter is attached. The device comprises a peristaltic pump, an ultra-filtration filter and a possibility of introducing anticoagulant into the system. A section of the tube system is guided through a heating bath in order to be able to compensate for temperature losses of the blood. The double-lumen catheter has an open tip communicating with one lumen. The first lumen and a second lumen communicate with lateral openings in the catheter wall.

Multi-lumen balloon catheters of varying design belong to the state of the art.

A multi-lumen balloon catheter with a closed tip is known from U.S. Pat. No. 4,382,688, having, at a short distance from the proximal end of the catheter, an expandable balloon communicating with one catheter lumen. On the proximal side of the balloon, in the catheter wall, there is a lateral opening which communicates with a second catheter lumen. At the rear end the catheter has an attachment piece in order to be able to establish connections with the individual lumina. The catheter can also have several balloons, lateral openings then being present in each case between two balloons.

In DE-A-3,821,544 a balloon catheter is described, the expandable balloon of which has a plurality of pore-shaped through-holes, so that material present inside the balloon can escape upon dilation. This material should exert its action in the area of the contact surface of the balloon with the vessel wall.

A further multi-lumen balloon catheter for drainage purposes is known from U.S. Pat. No. 3,394,705. The catheter has lateral openings both between the tip and the balloon, and also on the proximal side of the balloon, which lateral openings communicate with catheter lumina.

2. Description of the Related Art

In the treatment of tumours the action of cytostatic agents used depends on the local concentration and the pH value. The ability of the tumour cell to form colonies drops sharply in a concentration range of around 10 µg/ml. A high efficacy in the inhibition of tumours is therefore only achieved in this range, it being possible to achieve a further significant increase in the action of the cytostatic agent by means of a still higher concentration, up to a maximum of approximately 100 µg/ml.

In conventional systemic chemotherapy, the concentration of cytostatic agents is limited to 1–2 µg/ml. An increase to the abovementioned range in order to achieve a high tumour toxicity is not possible in this method on account of the systemic side-effects which occur.

SUMMARY OF THE INVENTION

The aim of the present invention is to provide a device which permits the administration of locally high concentrations of a therapeutically active substance. In particular, the device should permit the administration of high concentrations of cytostatic agents for chemotherapy in the range of over 10 µg/ml.

This aim is achieved according to the present invention by means of a multi-lumen balloon catheter with a closed tip and an expandable balloon arranged at a short distance from the proximal end of the catheter, with at least one contrast marking at one location on a catheter, which marking permits a determination of the position of the balloon, with at least two lumina extending parallel in the longitudinal direction of the catheter, of which one communicates with the inside of the expandable balloon and the second lumen has a number of lateral openings in the catheter wall, characterized in that the distance of the lateral openings increases in the distal direction from the balloon, and the proximal opening is arranged at a distance of 2 mm to 5 mm from the distal end of the balloon.

In a preferred embodiment of the present invention, a third lumen open at the end can moreover be provided. This opens into a flexible tube piece which is placed on the catheter tip and is used for receiving a guide wire during positioning of the catheter in the blood stream.

The solution also includes a device for the isolated perfusion of therapeutically active substances, comprising a pump system for infusion of the therapeutically active substance and a circulation system which comprises a three-way cock for attachment to the pump system, a pump system for the perfusion, two connection pieces for external attachment, and two sterile-packed tube pieces which can be connected to two balloon catheters according to the invention.

The catheter according to the present invention comprises a balloon with a filling volume of a maximum of 25 ml for blocking a main artery or vein, such as, for example, the aorta or the vena cava.

The catheter has a contrast marking, which can be detected by X-ray, at a suitable point in order to permit an exact positioning in the blood vessel under image converter monitoring. In a preferred embodiment the balloon is bordered by X-ray contrast markings on the edges of the balloon. The contrast marking is obtained by incorporating radio-opaque pigment in the polymer material of the catheter tubing at the desired points. It is additionally possible also to fill the balloon with a radio-opaque fluid for expanding the balloon and in this way to improve still further the monitoring of the position. The X-ray contrast medium is introduced through the filling lumen of, the catheter, which is provided at the end with a stopcock. Extending parallel to the filling lumen for the balloon is an infusion lumen, which has a number of lateral openings starting from a distance of 2–5 cm from the distal balloon end. These openings have an increased spacing in the distal direction from the balloon. In a preferred embodiment of the present invention, the lateral openings are arranged at 4 different distances from the balloon, in such a way that they are separated from one another in each case by approximately 10, 20 and 40 mm.

This arrangement prevents an overdosage of the cytostatic agent through branches of the blood vessel lying near the opening, and thus an excessive or inadequate therapy of individual areas to be treated. The lateral openings generally have a round or oval shape and have a diameter of 1.5–3 mm.

The catheter according to the invention is required in a harder and a softer design form. Preferred materials for the harder design form are medically compatible plastics such as polyethylene, polypropylene, polyvinylchloride, polyurethanes, polycarbonates, polyamide and silicone elastomers.

The polymer material has a Shore A hardness of 96–99.

For the softer design the same plastics are suitable as for the harder form, but in a softer format with a Shore A hardness of 87–95.

The catheter is closed at its tip. The infusion lumen of the catheter is provided at its distal end with a three-way cock in order to permit the separate infusion successively of two identical or different fluids.

It is particularly preferable to provide the catheter according to the present invention with a third lumen. This is used as a lumen for a guide wire and facilitates the positioning of the catheter in the blood vessel. The third lumen opens proximally into a terminal tube piece which is placed in a suitable manner on the tip of the catheter. In order to permit the insertion of the wire, the tube piece is open at its end. The length of the tube piece amounts to 5–8 cm, measured from the upper edge of the balloon. In its upper third, the tube piece can be designed at an angle, the angle of deviation from the longitudinal axis of the catheter being generally between 20° and 30°.

The distal end of the insertion lumen has a three-way cock or else a self-closing valve.

Whilst the third lumen is made from the same materials as the rest of the catheter, the terminal tube piece is preferably made from soft, flexible materials.

Preferred materials for the tip are silicone elastomers, polyurethanes, polyolefins, PVC. This polymer material has a Shore A hardness of 80–85.

In order to achieve the desired high local concentration of cytostatic agent in the areas of the body to be treated, the treatment involves introducing the harder form of the double-lumen balloon catheter into a main blood vessel, for example the aorta, and interrupting the blood stream at a suitable point. For this purpose, a sufficient quantity of a fluid medium, for example a mixture of X-ray contrast medium and physiological saline solution, is introduced into the balloon through the filling lumen, and the catheter is fixed in the blood vessel by means of the expanded balloon. The filling volume is generally 20 to a maximum of 25 ml, and the desired quantity is set using the stopcock. By means of the radio-opaque markings, an exact positioning of the catheter is possible by image converter monitoring. The catheter according to the invention must be sufficiently rigid so that it is not kinked by the blood stream. This is achieved by using a harder polymer for the catheter tubing.

It is substantially more advantageous, however, first to introduce a guide wire into the blood vessel of the patient. On this the catheter is then introduced into the blood vessel by means of the discussed third lumen, the insertion lumen. Such a procedure greatly facilitates the positioning. Particularly when the catheter has to be pushed through significantly curved blood vessels such as, for example, the frequently sigmoid iliac artery, this therefore permits a safe insertion without perforating the vessels.

For this reason there is also the advantageous angular positioning, according to the invention, of the terminal tube piece of the balloon catheter according to the present invention.

After inserting the balloon catheter according to the invention into the blood vessel supplying blood to the thigh of a patient, the venous return is greatly reduced or interrupted by means of pneumatic cuffs before the cytostatic agent and a standard solution are introduced into the blood vessel in a suitable manner through the infusion lumen using the three-way cock.

After a maximum treatment time of 15 minutes the blood vessel and the leg cuffs are successively loosened and removed.

The use, as discussed above, of the catheter according to the invention gives satisfactory results in many cases. However, the stoppage of the blood, effected by blocking the systemic circulation, in the area of the body treated can have disadvantageous effects. Despite the special design of the catheter according to the present invention, local differences in the concentration of the pharmaceutical agent can occur in the area to be treated, even though these are substantially less than when using a catheter which does not have the specially devised arrangement of the lateral outlet openings.

In order to avoid disadvantages of this type, it is possible, with a device having two catheters, to apply a blood plasma circulation to the isolated area of the body to be treated.

In this case, as described above, the catheter according to the present invention is fixed in a blood vessel, for example an artery. Thereupon, a second catheter made of softer material is introduced into a corresponding main vein, for example the major vein of the body (vena cava), and is fixed at a suitable place, as described above, in order to lead off venous return from the area of the body to be treated.

The infusion lumina of the catheter are connected via suitable devices to a so-called perfusion system. This perfusion system comprises a pump device with which an isolated blood circulation can be operated in the area of the body to be treated. Any air bubbles are removed from the system by means of an air trap. By means of a further pump, the infusion fluid with the pharmacologically active substance, for example a cytostatic agent, is introduced into the area of the body to be treated through the catheter according to the invention.

After the perfusion system has been connected to the two catheters, and the venous return from the area of the patient's body to be treated to the heart has been interrupted, the cytostatic solution is infused for 3 to 4 minutes and the pump device of the perfusion system is set in operation, as a result of which an isolated blood circulation develops and the infused cytostatic agent is distributed homogeneously in the area of the body to be treated.

It goes without saying that in this case no cytostatic agent is introduced through the perforations of the second soft catheter fixed in the vein, but instead blood is removed from the vein and is taken up by the perfusion system for renewed delivery into the first catheter and for homogeneous distribution in the area to be treated.

In this treatment method too a catheter must be used which has the special arrangement of the lateral openings. It has been shown that otherwise, despite the pump system, brief local excess concentrations can arise, as a result of which systemic side effects can occur.

This hypoxic perfusion can be performed for 15 minutes, so that the duration of action of the cytostatic agent is significantly reduced from the customary 60 minutes without any resulting loss in efficacy.

Furthermore, as a result of the hypoxic treatment method, the oxygen content of the body areas isolated by the blocking falls. However, since this results in a drop in the pH value, the efficacy of some cytostatic agents, which respond better in the slightly acid range than in the neutral range, is thereby increased.

However, it is also possible to arrange in the perfusion system an oxygenator with heat exchanger in order to enrich the blood circulation with oxygen. The thereby achieved hyperthermal perfusion with oxygenation has the advantage that the cytostatic exposure can be maintained for a longer time, up to approximately 2 hours.

Similarly, the perfusion system according to the present invention can comprise devices which permit the attachment of a filtration set. Such a filtration set permits the removal, after treatment, of high concentrations of cytostatic agent constituting a systemic burden on the patient. Known filtration systems with membrane filters can be used. The filtration is carried out before the blocking action of the balloons is ended and the separate perfusion circulation is opened to the systemic circulation.

DESCRIPTION OF THE PREFERRED EMBODIMENT

The invention will now be described in greater detail with reference to the drawings.

Figure 1:
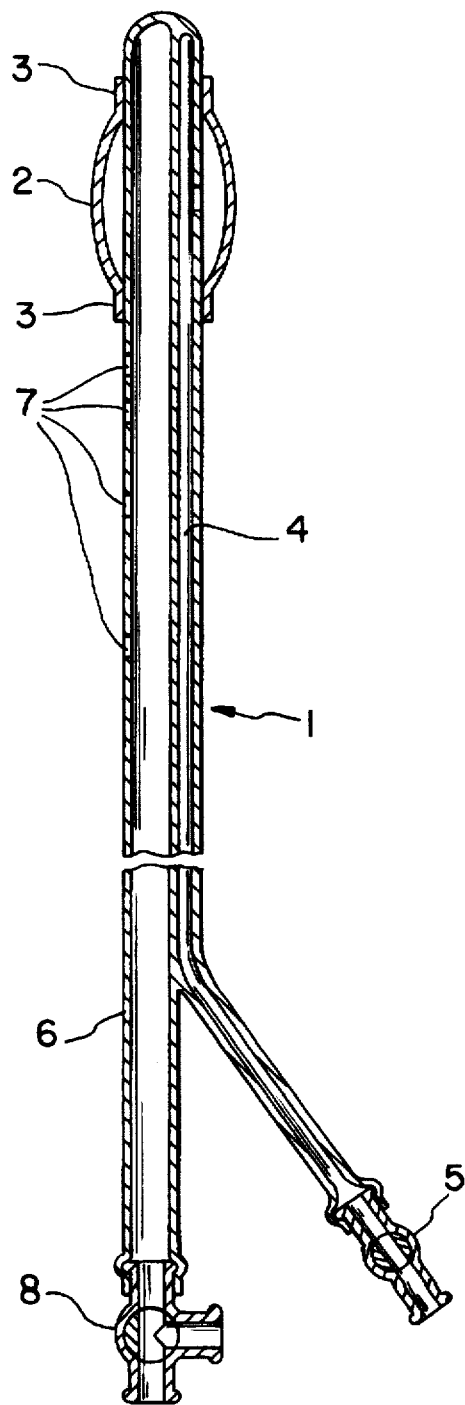
FIG. 1 shows a front elevational view of a catheter according to the instant invention.

FIG. 1 shows a preferred embodiment of the catheter according to the present invention. The catheter 1 has a closed tip. Arranged at a short distance from this, on the outer side of the catheter tubing, is an expandable balloon 2 having a volume of approximately 20–25 ml. The balloon 2 can be supplied via the lumen 4 with a fluid for expansion. The stopcock 5 is used for closing the lumen 4. The so-called infusion lumen 6 is used for supplying active substances, for example a cytostatic agent. It has four lateral openings 7 in the catheter wall, which are arranged, in the distal direction from the distal end of the balloon 2, at a progressively increasing distance of approximately 10, approximately 20 and approximately 40 mm. The infusion lumen 6 has, at its peripheral end, a three-way cock 8. The X-ray contrast markings beside the balloon 2 are indicated by the number 3.

Figure 2:
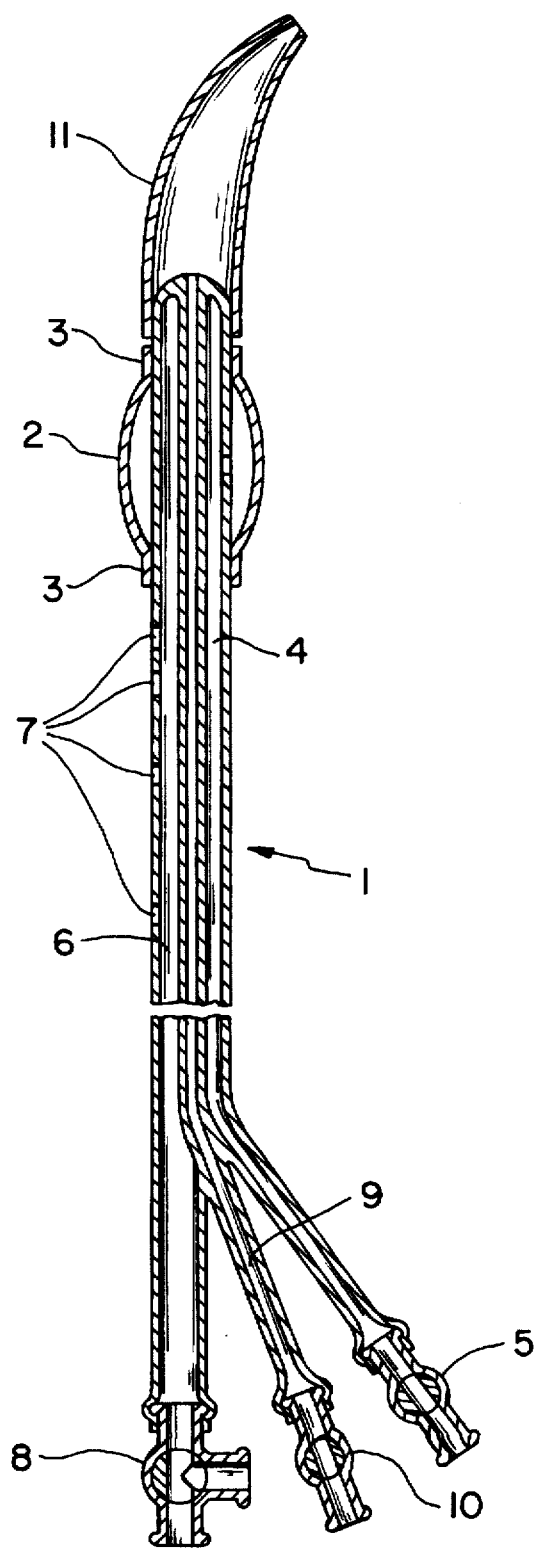
FIG. 2 shows another embodiment of a catheter according to the present invention.

FIG. 2 shows a further embodiment of the catheter according to the present invention. This catheter corresponds in its design to the catheter described in FIG. 1, but it has a third lumen 9. This extends parallel to the filling lumen 4 and the infusion lumen 6 and has, at its distal end, a stopcock or a self-closing valve 10. The third lumen 9 opens into an open, terminal tube piece 11, which is situated on the tip of the catheter 1. This tube piece is approximately 5–8 cm long, measured from the front X-ray contrast marking 3, and is bent in the front third by an angle of approximately 20°–30°.

Figure 3:
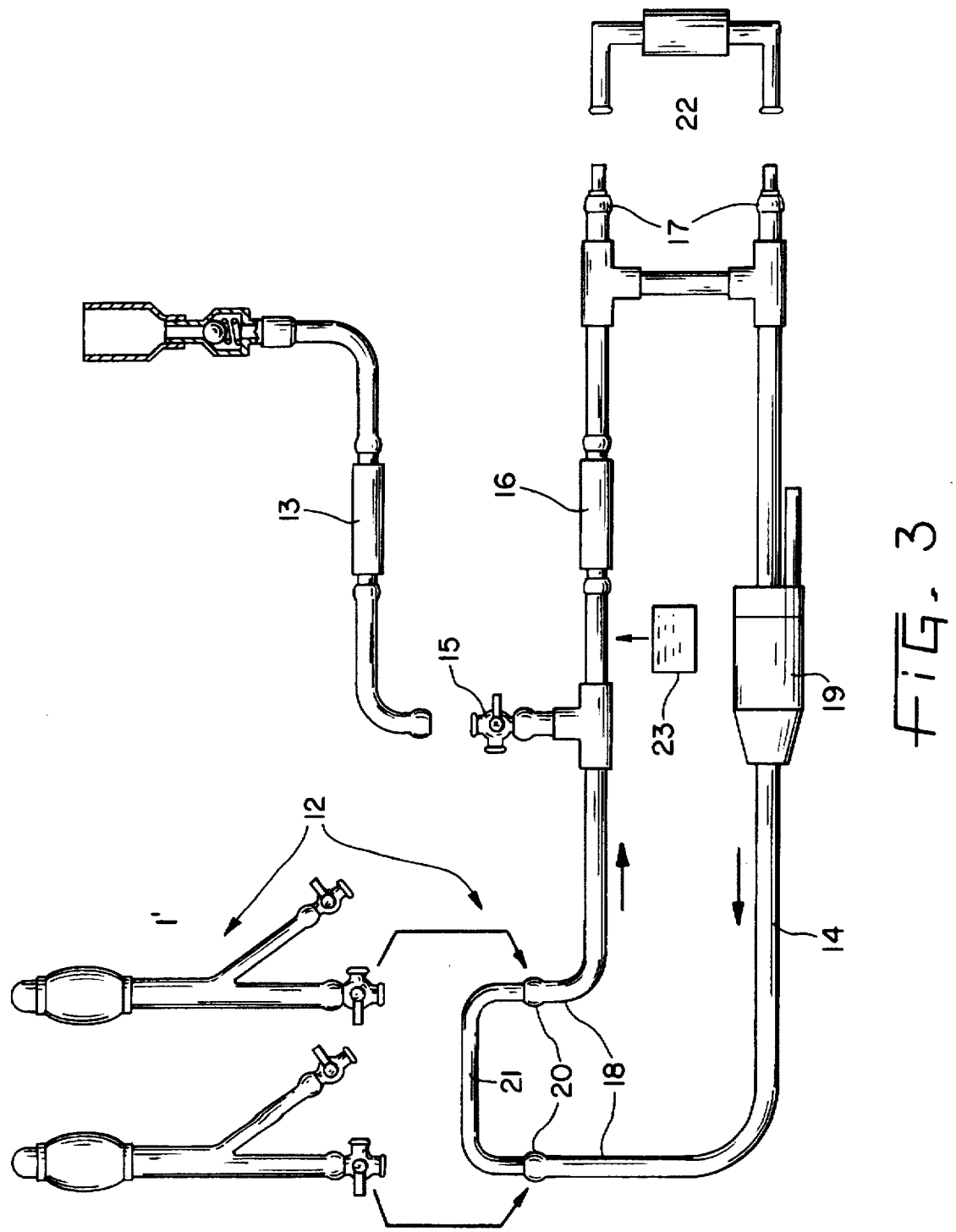
FIG. 3 shows a closed perfusion system according to the present invention.

FIG. 3 shows an embodiment of the closed perfusion system according to the present invention. This perfusion system 12 comprises two connection pieces 17, which are used for filling the system and for possible attachment of a filtration set 22, a pump system 16 for the perfusion, an air trap 19 for collecting air bubbles in the system, two tube pieces 18 and a further three-way cock 15. The tube pieces 18 are attached at the two connectors 20 to the infusion lumina 6 of the catheters 1,1' via the three-way cock 8, after the tube connection piece 21, which initially connects the two connectors 20, has been removed. The three-way cock 15 is used for introducing the cytostatic solution into the perfusion circulation by means of a further pump system 13.

In an alternative embodiment of the invention, an oxygenator with heat exchanger 23 can be arranged between the three-way cock 15 and the pump system for the perfusion 16.

In a further alternative embodiment of the present invention, a filtration set 22 can be connected via the connection pieces 17 to the perfusion circulation for the purpose of removing high concentrations constituting a potential systemic burden on the patient.

Such a filtration set 22 is represented in FIG. 4 of DE-A-3,400,874 and is described. This device is designed for attachment to double-lumen catheters, the suction line being attached to the tube and the return line being attached to the tube. From the outer tubing of the catheter, venous blood is sucked through the tube connection by the peristaltic pump and is forced through the adjoining tube into the ultrafiltration filter and arrives from there through the tube connection into the inner tubing of the catheter. Opening into the tube connection, in front of the filter, is the supply line for anticoagulant which arrives from an automatic injection apparatus. Connected into the tube connection, in front of and behind the peristaltic pump, are in each case rubber membranes for use of injection syringes to take samples. These same rubber membranes are present in the filtrate line between the filter and the valve and in the tube line behind the coil arranged in the water bath.

The filtrate line extends from the ultrafilter, in which line the precisely adjustable valve is arranged and which line ends in a measuring vessel for collecting the filtrate. The measuring vessel has an index and a capacity of 1–3 liters. Situated behind the ultrafiltration filter, in the tube connection, is the admission point for replacement fluid, which is introduced by a second peristaltic pump. The peristaltic pump sucks the replacement fluid from one or more storage vessels of sufficient size which are joined via tube connections. If appropriate, branches are present in the tube connection by means of T-pieces in order to be able to use a number of different replacement fluids. The pumping-in of the replacement fluid, for which so-called Ringer solutions are preferably used, is necessary because otherwise the large quantities of replacement fluid cannot be introduced into the system with the desired accuracy and speed. The output of the second peristaltic pump is set to the quantity of fluid emerging from the system through the adjustable valve in such a way that in terms of volume a lose of fluid is avoided as far as possible. However, in principle, it is also possible to introduce smaller or larger quantities of replacement fluids, if this is necessary in a particular case in the context of general treatment.

In order to compensate for cooling losses, a tube coil is preferably arranged in the tube line, which coil is situated in a water bath which is at a temperature of approximately 40°. In this way heat losses which occur can be compensated in a simple manner so that the retentate can be returned to the vein at the desired temperature after filtration. The tube connection between the catheter and the peristaltic pump has a length of approximately 1.5 m, the tube distance between the peristaltic pump and the filter amounts to approximately 1 m, and approximately 2-m tube connections without the tube coil are necessary for the attachment of the tube to the catheter. The tube connections have an internal diameter of approximately 5 m and an external diameter of approximately 7 mm.

The attachment points of the two-way attachment piece have, like the tubes, coloured markings, for example red and blue, in order to avoid confusion during attachment.

The overall device is designed as a so-called filtration set together with the catheter. The set is preferably marketed complete, with a sterile packing being preferred, so that the whole combination is ready for immediate use. In principle, however, it is also possible to divide the set into sterile-packed components and components which are not sterile-packed.

LIST OF REFERENCES 1,1' Catheter
2 Balloon
3 X-ray contrast marking
4 Filling lumen
5 Stopcock
6 Infusion lumen
7 Openings
8 Three-way cock
9 Insertion lumen
10 Self-closing valve, stopcock
11 Terminal tube piece
12 Perfusion system
13 Pump system for infusion
14 Circulation system
15 Three-way cock for infusion attachment
16 Pump system for perfusion
17 Connection pieces
18 Tube pieces
19 Air trap
20 Connectors
21 Tube connection piece
22 Filtration set
23 Oxygenator with heat exchanger

I claim:

1. Multi-lumen balloon-type blocking catheter having a side wall a proximal end, and a distal end, said catheter comprising: a closed tip at said proximal end, an expandable balloon arranged at a short distance from said proximal end, a contrast marking at one location on the catheter to permit determination of the position of the balloon, at least two lumens extending in the longitudinal direction of the catheter, the first said lumen communicating with the inside of the expandable balloon for filling and expanding said balloon, the second said lumen terminating in said closed tip, said second lumen further having a number of lateral openings in the catheter side wall arranged serially in the longitudinal direction of the catheter, a first said lateral opening spaced a distance of 2 mm to 5 mm from the balloon in the direction toward the distal end of the catheter, the distance between successive adjacent lateral openings progressively increasing in the direction toward the distal end of the catheter.

2. The catheter according to claim 1, wherein the lateral openings have one of a round and an oval shape, with a diameter of 1.5 to 3.0 mm.

3. Balloon catheter according to claim 2, wherein four lateral openings are provided, said lateral openings respectively spaced from one another by approximately 10 mm, 20 mm and 40 mm.

4. Balloon catheter according to claim 2, wherein a three-way valve is arranged at the distal end of the second lumen.

5. Balloon catheter according to claim 1, wherein four lateral openings are provided, said openings respectively spaced from one another by approximately 10 mm, 20 mm and 40 mm.

6. Balloon catheter according to claim 3, wherein each said lateral opening comprises a plurality of apertures.

7. Balloon catheter according to claim 5, wherein a three-way valve is arranged at the distal end of the second lumen.

8. Balloon catheter according to claim 1, wherein each said lateral opening comprises a plurality of apertures.

9. Balloon catheter according to claim 1, wherein a three-way valve is arranged at the distal end of the second lumen.

10. Balloon catheter according to claim 1, wherein the catheter includes an open tube at its proximal end connected to said closed tip, and a third lumen connected to and opening into said open tube.

11. Balloon catheter according to claim 10, wherein said open tube has a length of 5–8 cm, measured from said contrast marking.

12. Balloon catheter according to claim 10, wherein approximately one third of said open tube is bent at an angle of 20°–30° with respect to the longitudinal axis of the catheter.

13. Balloon catheter according to claim 10, wherein said open tube is made from a polymer having a Shore A hardness of 80 to 85.

14. Balloon catheter according to claim 1, wherein the catheter is made from a polymer having a Shore A hardness of 92 to 96.

15. Balloon catheter according to claim 1, wherein the catheter is made from a polymer having a Shore A hardness of 87 to 90.

16. Apparatus for the isolated perfusion of therapeutically active substances, comprising an infusion pump for infusion of a therapeutically active substance connected to a circulation system by a three-way valve, a perfusion pump connected to said circulation system, two connection pieces connected to said circulation system for attachment of the apparatus to external devices, two tube pieces connected to said circulation system, and two balloon catheters according to claim 1 respectively connected to said two tube pieces.

17. Apparatus according to claim 16, wherein the two balloon catheters are respectively composed of materials of different hardnesses.

18. Apparatus according to claim 16, wherein the circulation system furthermore comprises an oxygenator with a heat exchanger.

19. Apparatus according to claim 16, wherein a filtration set for purifying blood is connected to said connection pieces.

* * * * *